US00PP08104P

United States Patent [19]

Jessel, Jr.

[11] Patent Number: Plant 8,104

[45] Date of Patent: Jan. 19, 1993

[54] CARNATION PLANT NAMED CFPC MAJESTIC

[75] Inventor: Walter H. Jessel, Jr., Salinas, Calif.

[73] Assignee: California Florida Plant Co., L.P., Salinas, Calif.

[21] Appl. No.: 676,810

[22] Filed: Mar. 28, 1991

[51] Int. Cl.[5] ..... A01H 5/00

[52] U.S. Cl. ..... Plt./70.5

[58] Field of Search ..... Plt./70-71, Plt./70.2, 70.1, 70.5, 70.6, 71.1

[56] References Cited

U.S. PATENT DOCUMENTS

P.P. 1,437 12/1955 Sim ..... Plt. 73

P.P. 5,545 8/1985 Hilverda ..... Plt. 71

OTHER PUBLICATIONS

Plant Patent Directory, 1990 by the American Association of Nursery. p. 40 Numerical Listing of Patents, pp. 18-22 Alphabetical Listing of Patents.

*Primary Examiner*—Howard J. Locker

*Attorney, Agent, or Firm*—Christie, Parker & Hale

[57] ABSTRACT

A new and unusual carnation of orchid pink coloration.

1 Drawing Sheet

SUMMARY OF THE INVENTION

The present invention relates to a new and distinct cultivar of carnation plant which was discovered by me in a controlled planting of seedlings of my creation. The new variety is a mutation of an unnamed and unpatented seedling of my creation which was a cross of another one of my seedlings, (No. 001790), as seed parent with the variety known as 'Trio' as pollen parent. The varietal denomination of the new variety is CFPC Majestic.

CFPC Majestic is a carnation plant producing sprays of attractive pink coloring. The parent seedling, of which the new variety is a mutation produced cream colored flowers with an orchid picotee edge.

Among the novel characteristics possessed by the new variety which distinguishes it from its parents and all other varieties of which I am aware are its flowers of unusual orchid pink coloring that holds well, and smooth petal edge in the sense the edge is not notched or serrated, yielding a dainty flower appearance. Flowers of the new variety have a vigorous fast breaking habit with numerous laterals and high bud and flower count per stem. The flowers are small, spray-type and open fully without bursting the calyx causing "splits". Flower response of the new variety is about 15 weeks from planting to flowering.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety depicted in color as nearly true as it is reasonably possible to make the same in a color illustration of this character.

DESCRIPTION OF THE NEW VARIETY

The new variety, CFPC Majestic, has a high production rate of about 7 to 8 flowers per stem. CFPC Majestic also exhibits a fast response about 15 weeks, which, together with its attractive orchid pink coloring and the other characteristics heretofore and hereinafter described, make it especially suitable for commercial cut flower production as sprays.

The following is a detailed description of my new variety, with color terminology in accordance with The Royal Horticultural Society Color Chart (R.H.S.C.C.). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, Calif. The height of plant and flower and foliage size are established as an average using standard commercial cultural practices.

Name: CFPC Majestic.

Classification:

*Botanical.*—*Dianthus caryophyllus.*

*Commercial.*—Carnation, spray type.

Parentage: Mutation of an unnamed, unpatented seedling.

Plant:

*Height.*—About 39 inches.

*Growing habit.*—Herbaceous, semi-upright.

*Blooming habit.*—Terminal as a spray.

*Blooming season.*—Year round.

*Rooting time.*—16 to 17 days.

*Breaking action.*—Excellent.

*Mutation prone.*—No.

*Disease resistance.*—resistant to Rhizoctonia and Sclerotinia.

*Temperature tolerance.*—Typical for carnation.

Foliage:

*Color.*—Upper side: Near to 137B. Lower side: Near to 137C.

*Size.*—About 7 inches long, about ⅜ inch wide at base of plant.

*Quantity.*—Numerous.

*Shape.*—Lanceolate.
*Texture.*—Smooth.
*Ribs.*—Central, keeled.
*Arrangement.*—Bi-lateral along stem.
*Stems.*—Green.

Bud:
*Color.*—Near to from 137B to 137A before sepal separation.

Bloom:
*Form.*—Circular.
*Shape.*—Round.
*Size.*—Diameter average: About $1\frac{3}{4}$ to $2\frac{1}{4}$ inches. Depth average: About $1\frac{1}{8}$ inches.
*Borne.*—Terminally as a spray.
*Color.*—General tonality: Orchid pink. Upper side: Near to from 65C to 65D. Lower side: Near to from 65C to 65D. Center: Near to from 63C to 65C. Outer petals: Near to from 65C to 65D.
*Keeping Habit.*—Excellent.
*Fragrance.*—Very slight.

Petals:
*Number.*—Average about 32.
*Outer petals.*—Length: About $1\frac{3}{8}$ to $1\frac{5}{8}$ inches. Width: About 1 to $1\frac{1}{4}$ inches.
*Texture.*—Smooth, "satiny".
*Form.*—Fan shaped.

Reproductive Organs
*Ovaries.*—Shape: Conical. Color: Green.
*Styles.*—White base.
*Stigmas.*—Lavender pink.
*Filaments.*—Color: Pale lavender. Size: About $\frac{2}{3}$-inch.
*Anthers.*—Tan.
*Pollen.*—White.
*Fertility.*—Unknown.

I claim:

1. A new and distinct variety of carnation plant, substantially as shown and described, characterized particularly by flowers of attractive orchid pink coloration.

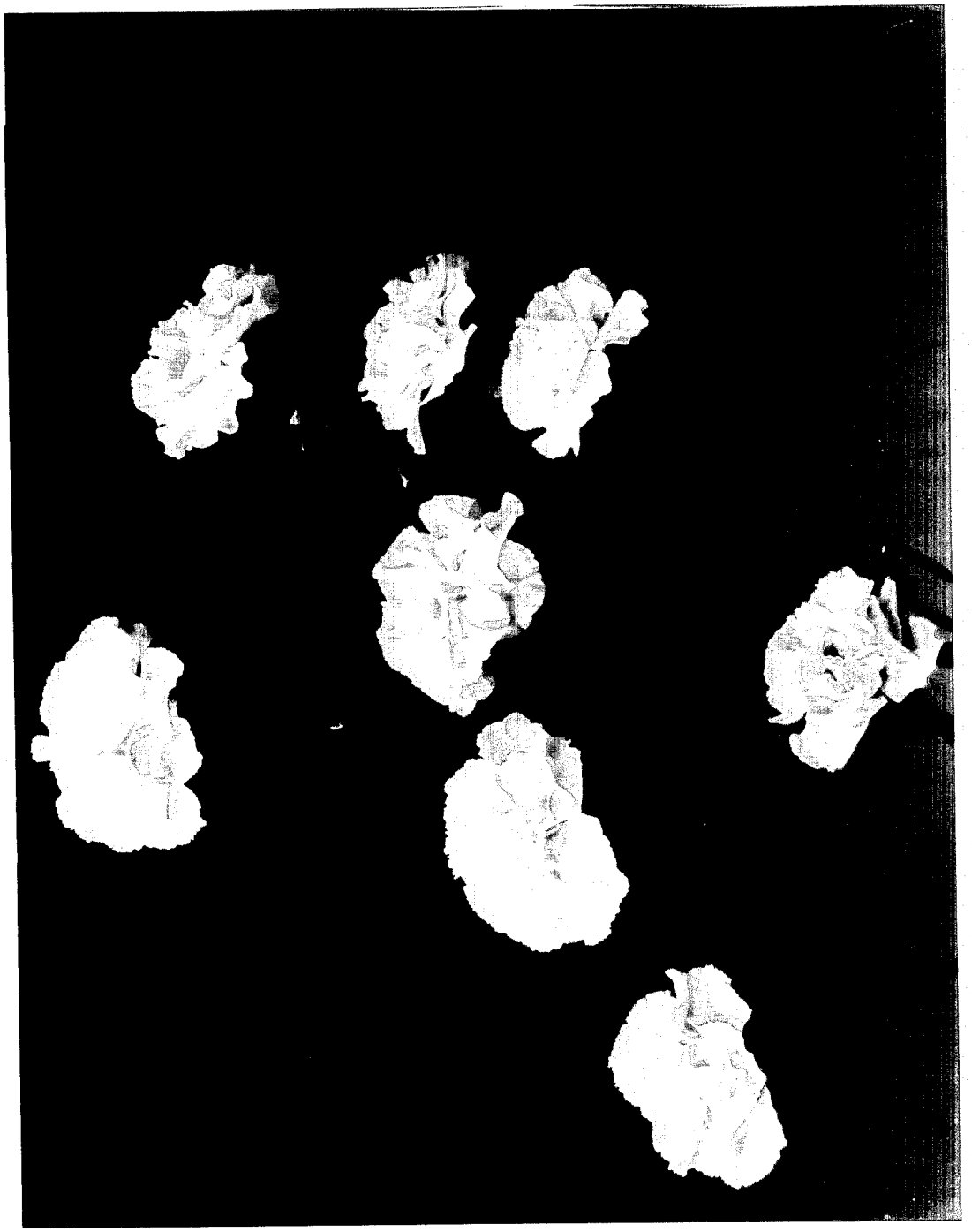

* * * * *